(12) United States Patent
Tandou et al.

(10) Patent No.: US 8,747,763 B2
(45) Date of Patent: Jun. 10, 2014

(54) PLASMA STERILIZATION APPARATUS

(75) Inventors: Takumi Tandou, Hachioji (JP); Nobuyuki Negishi, Tokyo (JP); Hiroyuki Kobayashi, Kodaira (JP); Keizo Suzuki, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 62 days.

(21) Appl. No.: 13/441,026

(22) Filed: Apr. 6, 2012

(65) Prior Publication Data
US 2012/0263628 A1    Oct. 18, 2012

(30) Foreign Application Priority Data

Apr. 13, 2011 (JP) ................................. 2011-089366

(51) Int. Cl.
*B01J 19/08* (2006.01)
(52) U.S. Cl.
USPC ................... 422/186.04; 422/186.07; 422/22; 204/164
(58) Field of Classification Search
CPC . A61L 2/14; H05H 1/2406; H05H 2001/2425
USPC ................... 422/186.04, 186.07, 22; 204/164
See application file for complete search history.

(56) References Cited

U.S. PATENT DOCUMENTS

2005/0179395 A1*    8/2005  Pai ........................... 315/111.21

FOREIGN PATENT DOCUMENTS

| JP | 1-242404 A | 9/1989 |
| JP | 2003-323964 A | 11/2003 |
| JP | 2005-211095 A | 8/2005 |
| JP | 2007-159821 A | 6/2007 |
| JP | 2008-289801 A | 12/2008 |

OTHER PUBLICATIONS

English translation of JP 01-242404.*

* cited by examiner

*Primary Examiner* — Xiuyu Tai
(74) *Attorney, Agent, or Firm* — Crowell & Moring LLP (57) ABSTRACT

In order to provide a plasma sterilization apparatus with high plasma generation efficiency, the apparatus includes first and second electrodes (3, 2), a first dielectric body layer (1), and an insulating spacer (6). The first dielectric body layer (1) is disposed between the first and second electrodes (3, 2). The insulating spacer (6) is disposed between the first electrode (3) and the first dielectric body layer (1). The insulating spacer (6) has a lower permittivity than a permittivity of the first dielectric body layer (1).

7 Claims, 8 Drawing Sheets

BEFORE PLASMA IRRADIATION

O2 PLASMA AFTER 10 min PLASMA IRRADIATION (30°C)

FIG. 5C

FIG. 6

| PROCESS TIME / PROCESS TEMPERATURE | 1min | 5min | 10min | 20min | 30min |
|---|---|---|---|---|---|
| 30°C | × | × | × | × | ○ |
| 87°C | × | × | × | ○ | ○ |

○ : INACTIVE
× : ACTIVE

※ STERILIZATION OBJECT : BACILLUS SUBTILIS (Geobacillus stearothermophilus), NUMBER OF BACILLUS 10^6

PLASMA STERILIZATION APPARATUS

CLAIM OF PRIORITY

The present application claims priority from Japanese patent application JP 2011-089366 filed on Apr. 13, 2011, the content of which is hereby incorporated by reference into this application.

BACKGROUND OF THE INVENTION

1. Field of the Invention

The present invention relates to a plasma sterilization apparatus that inactivates a floating fungus in the air (hereinafter referred to as an airborne *bacillus*).

2. Description of the Related Art

There are high expectations for realization of regenerative medicine, which uses an artificially cultured cell and tissue to regenerate damaged skin, corneas, organs and so on, so as to improve functional recovery of patients. The number of patients with the targeted diseases is estimated to 20,000 for corneal regeneration alone. Thus realization of this technology is desired. Participations of pharmaceutical companies are actualized, and it is expected that the regenerative medicine will make a new healthcare industry in the future.

Clinical research for regenerative medicine requires a biological clean room (hereinafter referred to as BCR), which allows aseptic manipulation. In order to maintain the indoor environment of BCR, it is necessary to establish sterilization technique, and this is an important issue. The conventional method for sterilizing inside BCR generally employs a method for sterilizing the whole indoor environment by reeking of formaldehyde inside the room. However, the formalin is harmful to human body because of as its carcinogenicity, for example. The use of formalin will be tend to be prohibited. In view of this, a sterilization technique using ozone instead of formalin has been proposed. Ozone generation techniques are disclosed in, for example, Japanese Patent Application Laid-Open Publication No. 1-242404 and Japanese Patent Application Laid-Open Publication No. 2003-323964. Bactericidal methods using ozone are disclosed in, for example, Japanese Patent Application Laid-Open Publication No. 2007-159821, Japanese Patent Application Laid-Open Publication No. 2005-211095, and Japanese Patent Application Laid-Open Publication No. 2008-289801.

SUMMARY OF THE INVENTION

In the sterilization in BCR, it is important to sterilize airborne *bacillus* so as to improve cleanness in the room. In order to study a new method for sterilizing the airborne *bacillus* in BCR, sterilization methods, which are generally used in a medical front or in a healthcare manufacturer, have been surveyed. The results are categorized as follows.

1) A filtration method using a HEPA filter or the like
2) A radiation sterilization method using a radiation (such as γ-ray), ultraviolet (with a wavelength of 254 nm), electron beam or the like
3) A gas sterilization method using Ethylene oxide gas, Hydrogen peroxide or the like As described above, various sterilization methods are available. However, it is probably difficult to apply these sterilization methods to sterilization of airborne *bacillus* in BCR. For example, a filtration method has difficulty in completely capturing floating bacilli that pass through a filter. The filtration method also has difficulty in sterilizing the captured bacilli in the filter. Thus, after a lapse of time, the bacilli may scatter from the filter into the air again. The radiation sterilization method provides weak sterilizing activity, thus requiring irradiation to the target bacilli to be sterilized for some tens of minutes to some hours. The problem arises in process time. The gas sterilization is harmful to human body similarly to the formalin and requires degassing for some hours to one day. Thus use of the gas sterilization tends to be avoided. In view of such background, a new sterilization method using plasma has been proposed as a new sterilization method that does not use harmful material and can process at low temperature and high speed.

First, plasma generating modules that generate ozone or the like have been surveyed regardless whether their intended purpose is sterilization or not. As a result, the survey has found a generally known dielectric-barrier system. The dielectric-barrier system is a plasma generating module that covers both a high-frequency electrode and an earth electrode with a dielectric body layer. This technique is also used for a plasma display panel (PDP) or the like. This technique is used in a wide range of use as a structure that provides low temperature plasma at atmospheric pressure with relative ease. However, the configuration generates a large amount of an electric power that is reactive and does not contribute to the plasma generation (hereinafter referred to as reactive power). Thus it is difficult to achieve power saving.

Japanese Patent Application Laid-Open Publication No. 1-242404 discloses a structure that covers only a high-frequency electrode with a dielectric body layer and includes an earth electrode disposed immediately above the high-frequency electrode. In view of this, it would appear that concentrated electrical lines of force pass through a plasma generation space (hereinafter referred to as a space). This enhances the electrical field strength in the space, thus increasing efficiently of the plasma. Further, Japanese Patent Application Laid-Open Publication No. 2003-323964 and Japanese Patent Application Laid-Open Publication No. 2008-289801 disclose a structure that includes a high-frequency electrode and an earth electrode disposed to sandwich a dielectric body layer. Thus structure has a discharge gap between the high-frequency electrode and the earth electrode. It would appear that this structure achieves a reduced reactive power passing through the dielectric body layer, compared with that of Japanese Patent Application Laid-Open Publication No. 1-242404. This increases the electric field strength in the space, thus ensuring high plasma generation efficiency. However, in the structures disclosed in Japanese Patent Application Laid-Open Publication No. 1-242404, Japanese Patent Application Laid-Open Publication No. 2003-323964, and Japanese Patent Application Laid-Open Publication No. 2008-289801, it is necessary to choose a dielectric body layer with a high permittivity to increase the electric field strength in the space. In principle, reactive current flows inside of the dielectric body layer, which generates the reactive power. In view of this, it would appear that there is a need for further improving the plasma generation efficiency.

Japanese Patent Application Laid-Open Publication No. 2007-159821 and Japanese Patent Application Laid-Open Publication No. 2005-211095 disclose that when a sterilization using ozone is performed, increasing temperature of bacilli in the sterilization improves sterilization effect. The above patent literatures disclose the methods that generate ozone using plasma or the like, control the temperature inside a chamber, to which the ozone is supplied, so as to heat the bacilli. This ensures sterilization at high speed. However, heating inside the chamber using ozone is insufficient and there is a need for improvement.

The present invention has been made in view of the above-described circumstances, and it is an object of the present invention to provide a plasma sterilization apparatus with high plasma generation efficiency.

According to one aspect of the present invention to achieve the above purpose, there is provided a plasma sterilization apparatus that includes first and second electrodes, a first dielectric body layer, and an insulating spacer. The first dielectric body layer is disposed between the first and second electrodes. The insulating spacer is disposed between the first electrode and the first dielectric body layer. The insulating spacer has a lower permittivity than a permittivity of the first dielectric body layer.

According to another aspect of the present invention, there is provided a plasma sterilization apparatus that includes a plasma generating portion and a flow path. The plasma generating portion includes first and second electrodes, a first dielectric body layer, and an insulating spacer. The first dielectric body layer is disposed between the first and second electrodes. The insulating spacer is disposed between the first electrode and the first dielectric body layer. The insulating spacer has a lower permittivity than a permittivity of the first dielectric body layer. The flow path is configured to provide fluid including a processing target of *bacillus* to a plasma region generated by the plasma generating portion. The flow path is arranged in an upper stream side of the plasma region such that the fluid cools the plasma generating portion.

With the present invention, an insulating spacer that has the lower permittivity than the permittivity of the dielectric body layer is disposed between the earth electrode and the dielectric body layer of the plasma generating module. This configuration provides a plasma sterilization apparatus that reduces reactive power and achieves high plasma generation efficiency.

BRIEF DESCRIPTION OF THE DRAWINGS

FIGS. 1A, 1B, and 1C are schematic diagrams illustrating configurations of conventional plasma generating modules;

FIGS. 2A, 2B, and 2C are explanatory diagrams of discharge characteristics of a plasma generating module;

FIGS. 3A, 3B, and 3C are schematic diagrams illustrating configurations of plasma generating modules of plasma sterilization apparatuses according to a first embodiment;

FIGS. 4A, 4B, and 4C are schematic diagrams illustrating other configurations of plasma generating modules of the plasma sterilization apparatuses according to the first embodiment;

FIGS. 5A, 5B, and 5C are explanatory diagrams illustrating a sterilization mechanism of oxygen radical;

FIG. 6 is a table of a sterilization effect of the oxygen radical;

FIG. 7 is a schematic diagram illustrating a configuration of a plasma sterilization apparatus according to a second embodiment; and FIGS. 8A and 8B are schematic diagrams illustrating sterile particles of the plasma sterilization apparatus according to the second embodiment.

DESCRIPTION OF THE EMBODIMENTS

As a result of studying conventional plasma sterilization apparatuses by the inventors, the followings have been found. A voltage applied for generating plasma provides a high electric field strength inside a dielectric body layer disposed between a high frequency applying electrode and an earth electrode while the voltage provides an low electric field strength outside the dielectric body layer. The low electric field strength outside the dielectric body layer contributes to plasma generation. Thus there is a need for increasing the electric field strength outside the dielectric body layer in order to improve plasma generation efficiency. As a result of studying a method to achieve this, the inventors have thought of providing a second dielectric body layer (an insulating spacer) between the earth electrode and the dielectric body layer that has a lower permittivity than that of the above dielectric body layer. The present invention has been made in view of the above-described circumstances. Embodiments of the present invention will be described in detail below.

[First Embodiment]

A first embodiment according to the present invention will be described below with a result of a study on conventional plasma generating modules.

FIGS. 1A, 1B, and 1C are schematic diagrams illustrating the configuration of the conventional plasma generating modules. In a plasma generating module that generates sterile particles such as ozone, as illustrated in FIG. 1A, a structure of a dielectric-barrier system is generally known. The dielectric-barrier system covers both a high-frequency electrode 2 and an earth electrode 3 with a dielectric body layer 1 (type 1). Type 1 is also used for a plasma display panel (PDP) or the like and is used in a wide range of use as a structure that provides a low temperature plasma at atmospheric pressure with relative ease.

Type 1 illustrated in FIG. 1A includes a portion where a distance between the high-frequency electrode 2 and the earth electrode 3 is smallest, that is, a region where concentrated electrical lines of force pass through. This provides a region with a high electric field strength inside the dielectric body layer 1. This causes a high reactive power passing through inside the dielectric body layer 1. On the other hand, plasma is generated by an electric field that leaks into a space through the dielectric body layer 1. In view of this, type 1 has a structure with a low plasma generation efficiency. Here, a reference numeral 4 designates a substrate, a reference numeral 5 designates a high-frequency power supply, a reference numeral 50 designates a plasma generating portion, and a reference numeral 60 designates a discharge gap. Identical reference numerals designate identical configurations.

FIG. 1B illustrates a structure that covers only the high-frequency electrode 2 with the dielectric body layer 1 and disposes the earth electrode 3 immediately above the high-frequency electrode 2 (type 2). Type 2 provides highly concentrated electrical lines of force 10 passing through a space so as to improve electrical field strength in the space. This achieves a reduced reactive power compared with type 1, thus generating plasma efficiently. However, similarly to type 1, a region where the electric field strength is highest is provided inside the dielectric body layer 1. Thus the plasma generation efficiency is not sufficient.

FIG. 1C illustrates a structure that includes a high-frequency electrode 2 and an earth electrode 3 sandwiching a dielectric body layer 1 and has a discharge gap between the high-frequency electrode 2 and the earth electrode 3 (type 3). This structure provides a region where the electric field strength is highest in the space. This further reduces reactive power than type 2 and increases the electric field strength in the space, thus generating plasma efficiently.

FIGS. 2A, 2B, and 2C are explanatory diagrams of discharge characteristics of a plasma generating module. FIG. 2A illustrates a device configuration for measuring the discharge characteristics. A direct current (hereinafter referred to as DC) power supply supplies DC power to an inverter with transformer. The inverter with transformer boosts the supplied DC power and supplies a High-frequency voltage Vpp to the high-frequency electrode 2 side of the plasma generating module. At this time, DC current and voltage of the DC power supply and the High-frequency voltage Vpp are measured.

Figure 1A:
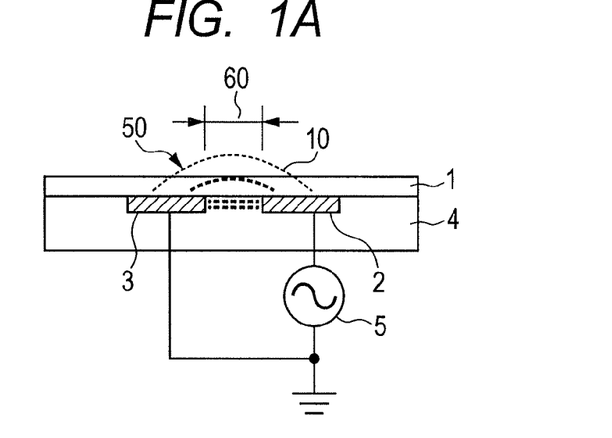
Figure 1B:
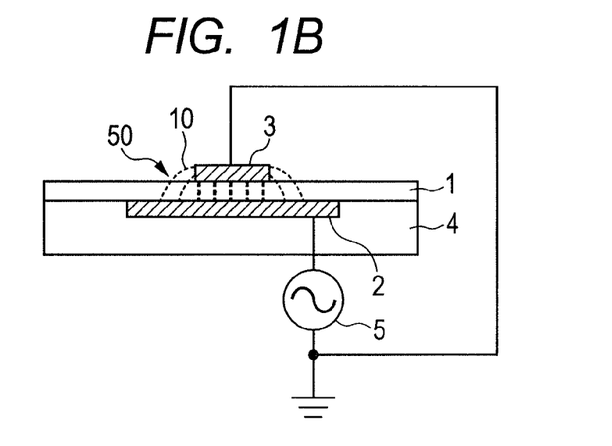
Figure 1C:
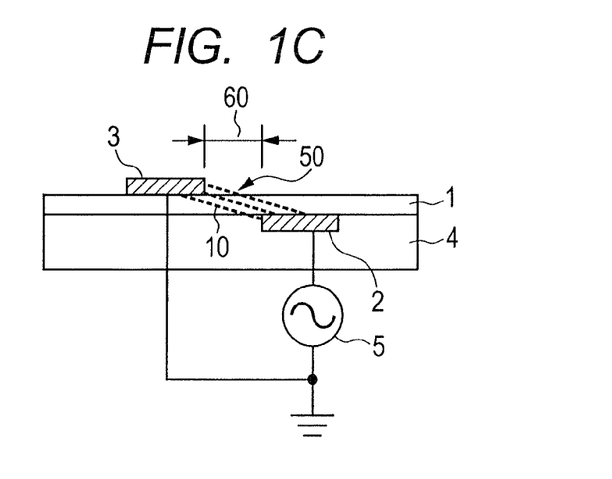
Figure 2A:
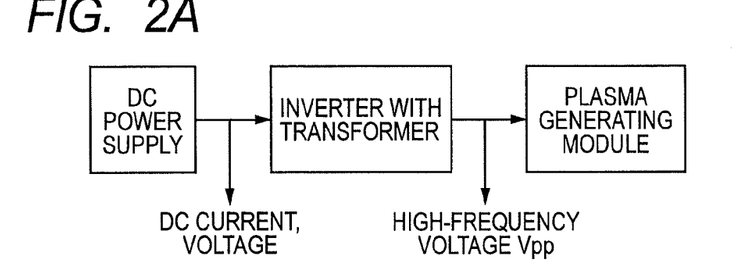
Figure 2B:
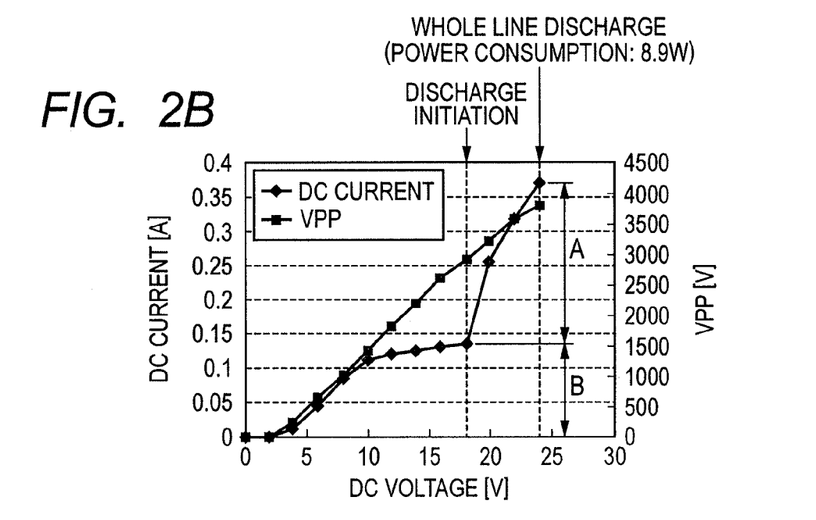

FIG. 2B illustrates a discharge characteristics of type 1 structure. Specifically, type 1 has a discharge gap of 100 μm and includes a dielectric body layer 1 with a film thickness of 20 μm. The dielectric body layer 1 is made of a soda glass with a relative permittivity $\in$ of 8. High-frequency voltage Vpp increases with increasing DC voltage, and the discharge is then initiated when the high-frequency voltage Vpp exceeds 3000 V. The DC current that flows before the discharge initiation is indicated as B region (0.13 A). This portion represents a reactive power. "A" region represents the electric power that went in the plasma itself.

Figure 2C:
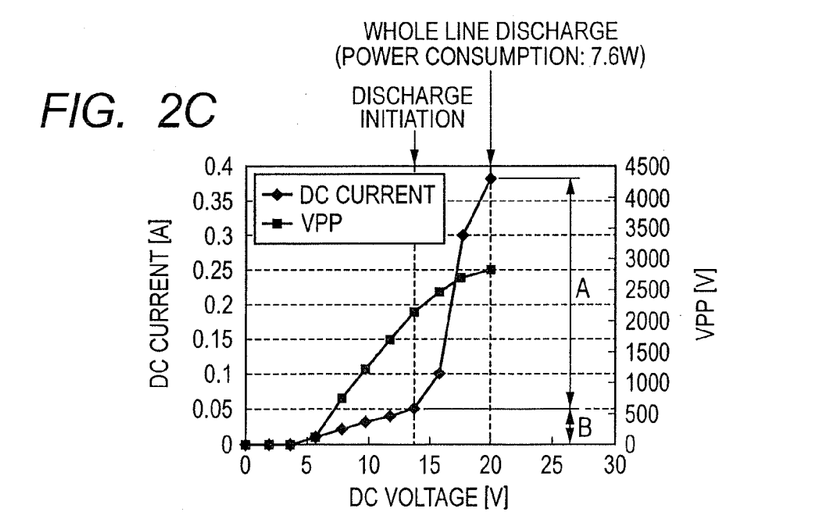

FIG. 2C illustrates a discharge characteristics of type 3 structure. Specifically, type 3 has a discharge gap of 100 μm and includes a dielectric body layer 1 with a film thickness of 100 μm. The dielectric body layer 1 has a relative permittivity $\in$ of 8. In order to increase voltage resistance of the dielectric body film, the dielectric body film is thicker than type 1 and the discharge is initiated when Vpp exceeds around 2100 V. The structure is configured to have an increased electric field strength in the space, compared with type 1. Thus plasma is generated with the low High-frequency voltage Vpp. This shows that the reactive current before the discharge initiation is 0.05 A. This reactive current is lower than a current of type 1.

Figure 3A:
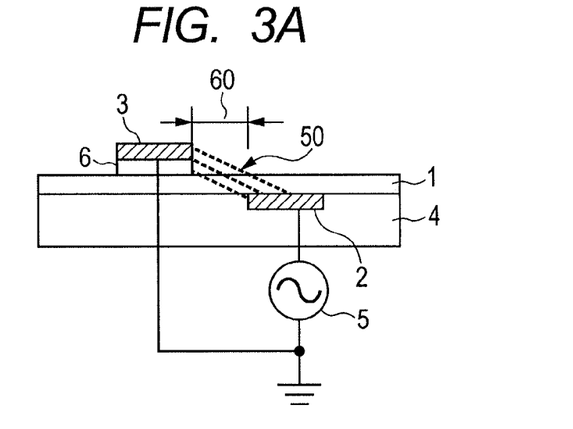
Figure 3B:
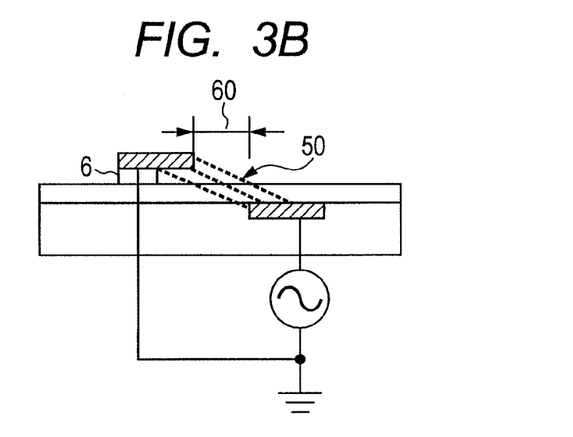
Figure 3C:
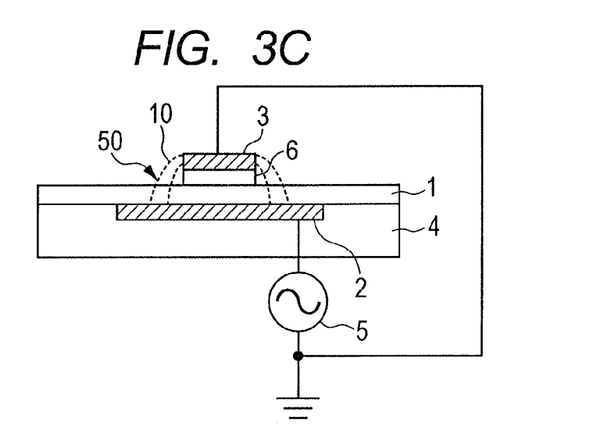

FIGS. 3A, 3B, and 3C are schematic diagrams illustrating configurations of plasma generating modules of plasma sterilization apparatuses according to the embodiment. FIG. 3A illustrates a first structure according to the embodiment. The first structure includes an insulating spacer 6 with a low permittivity disposed between a dielectric body layer 1 and an earth electrode 3. The high-frequency power supply 5 may employ a frequency of 10 kHz to 100 kHz. This reduces a reactive power flowing inside a dielectric body layer 1 further than type 3. This also facilitates the passing of electrical lines of force 10 in a space, thus reducing a discharge initiation voltage. If the insulating spacer 6 has a function as an adhesive layer when an earth electrode 3 is formed on the dielectric body layer 1, this configuration leads to both reduced reactive power and facilitated production. For example, a double sided tape made of organic material may be used. The material and the thickness of the insulating spacer 6 is specifically determined based on a plasma etching condition (for example, a etching gas, temperature, and pressure) and etching tolerance. Plasma in the atmosphere does not cause sputtering. This allows use of organic material. Instead of use of the double sided tape, patterning may be employed after forming a laminated film made of a dielectric body layer with a low permittivity and an electrode material layer.

FIG. 3B illustrates a second structure of the embodiment. A structure with a narrow insulating spacer 6 further reduces the reactive power that flows between the high-frequency electrode 2 and the earth electrode 3 through inside a dielectric body film. A space region of an inferior surface of the earth electrode 3 is allowed to be used as a plasma generation space. It is expected that there is an effect to increase plasma generation volume. However, in the case where the insulating spacer 6 has a too narrow width, the earth electrode 3 is not firmly installed. Thus the width of the insulating spacer 6 is preferably equal to or more than a half of the width of the earth electrode 3.

FIG. 3C illustrates an exemplary type 2 structure to which an insulating spacer 6 is applied. Disposing the insulating spacer 6 at a region where an electrical field strength is largest reduces reactive power and improves plasma generation efficiency further than type 2. However, compared with the first and second structures of the embodiment, the reactive power is still large.

Plasma sterilization apparatuses that include the plasma generating modules with the structures according to FIG. 3A to FIG. 3C were used for sterilization of the air in BCR. This showed that each of the structures reduces electric power and increases plasma generation efficiency further than the conventional structures.

Figure 4A:
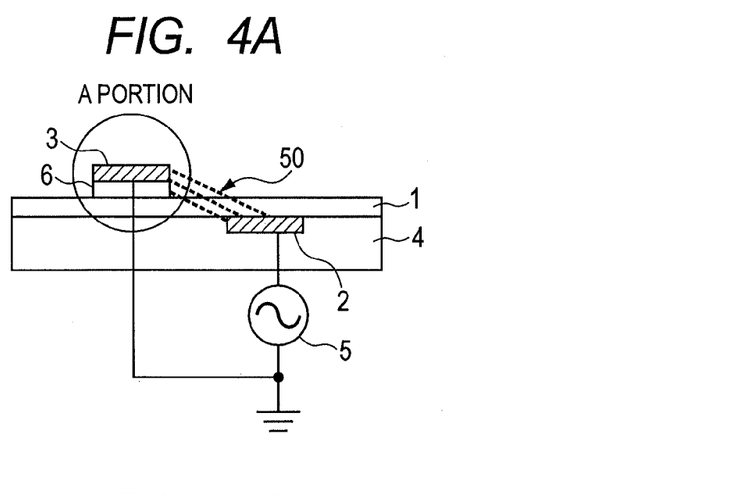
Figure 4B:
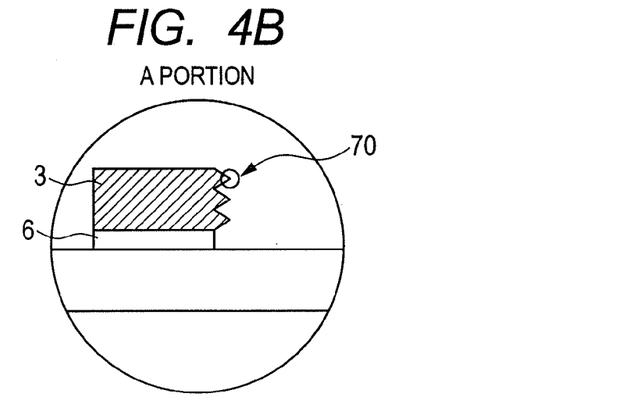
Figure 4C:
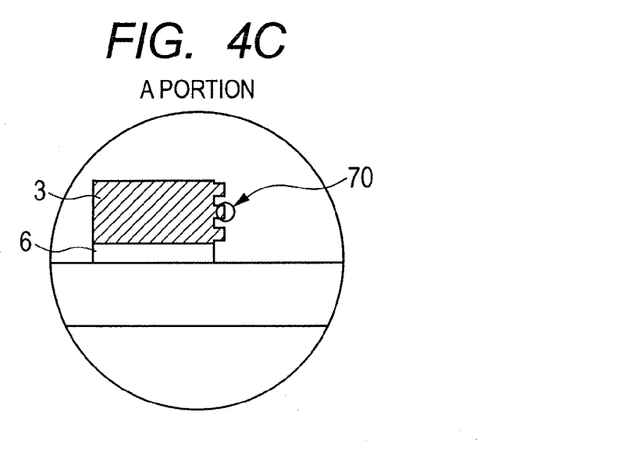

FIGS. 4A, 4B, and 4C are schematic diagrams illustrating other configurations of the plasma generating modules according to the embodiment. "A" portion of the first structure according to the embodiment illustrated in FIG. 4A will be described by referring to FIG. 4B and FIG. 4C in detail. FIG. 4B illustrates a structure that includes a projection on a side face of the earth electrode 3, which concentrates of an electric field at a distal end of the projection (an electric-field-concentrating portion 70). This reduces a discharge initiation voltage. FIG. 4C illustrates a structure that includes a protruding portion (an electric-field-concentrating portion 70) on the side face of the earth electrode 3, which concentrates an electric field, similarly to FIG. 4B. This reduces a discharge initiation voltage. Choose of the structures of FIG. 4B and FIG. 4C may be determined considering material or a producing method of the earth electrode 3. Both structures are formed by a known dry etching.

Plasma sterilization apparatuses that include the plasma generating modules with the structures according to FIG. 4B and FIG. 4C were used for sterilization of the air in BCR. This showed that each of the structures reduces electric power and increases plasma generation efficiency further than the structures according to FIG. 3A to FIG. 3C.

The embodiment that includes the second dielectric body layer (the insulating spacer 6), which has a lower permittivity than the dielectric body layer between the electrode and the dielectric body layer, provides the plasma sterilization apparatus with high plasma generation efficiency. The electric field concentrating portions disposed on the side face of the electrode improve plasma generation efficiency.

[Second Embodiment]

A second embodiment according to the present invention will be described below. Matters that are not described in this embodiment and described in the first embodiment may be also applied to this embodiment unless the circumstances are exceptional. The embodiment employs the module with the configuration according to FIG. 3A.

Figure 5A:
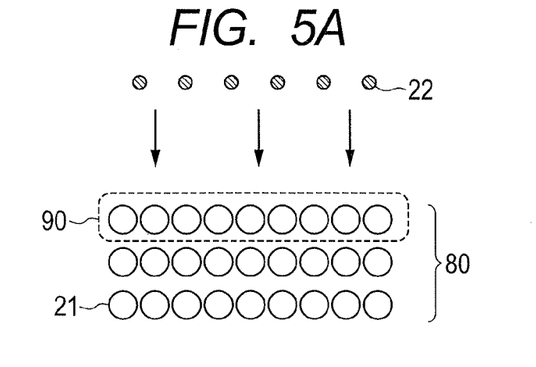
Figure 5B:
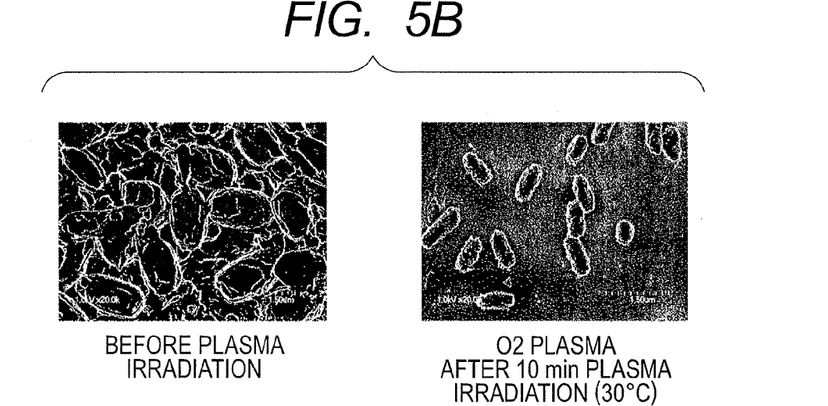
Figure 5C:
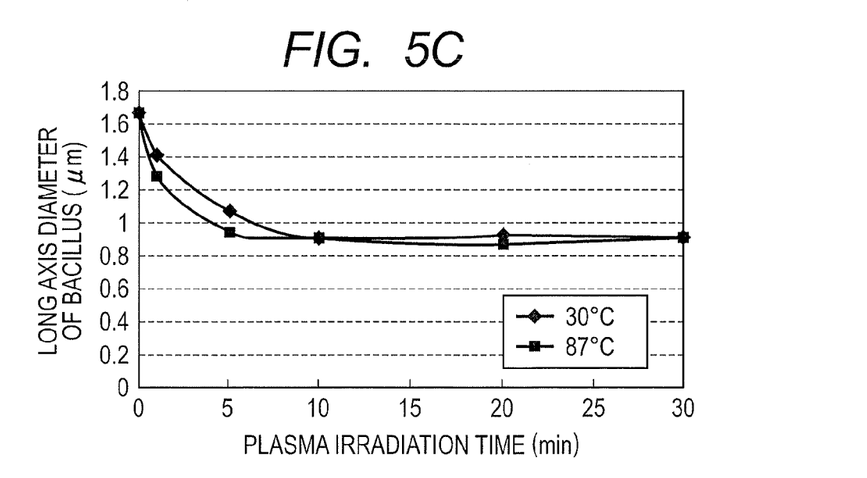

FIGS. 5A, 5B, and 5C are explanatory diagrams illustrating a sterilization mechanism of oxygen radical. It is known that the oxygen radical 22 has stronger oxidizing action than that of ozone and large sterilization effect. An experiment was carried out. The experiment irradiated *Bacillus subtilis* with the oxygen radical 22 generated by oxygen plasma. *Bacillus subtilis* (processing target of *bacillus* 21) (Geobacillus stearothermophilus, ATCC7953), which has the most tolerance to plasma sterilization. *Bacillus subtilis* is an indicator *bacillus* of plasma sterilization.

The number of *Bacillus subtilis* (processing target of *bacillus* 21) is $10^6$. This forms a colony (cluster) 80 as illustrated in FIG. 5A. Thus *Bacillus subtilis* (processing target of *bacillus* 21) undergoes oxidizing sterilization by the oxygen radical 22 gradually from a surface layer 90.

FIG. 5B illustrates an observational result of *Bacillus subtilis* (processing target of *bacillus* 21) observed through a scanning electron microscope (SEM) before plasma irradiation and after 10 min oxygen plasma irradiation. Oxygen plasma irradiation causes desorption of elements such as carbon (C) and oxygen (O), which are components of *Bacillus subtilis* (processing target of *bacillus* 21) with the oxygen radical 22 including the oxygen plasma. This shrinks the diameter of *bacillus*. The desorption results in destroying cell walls of *Bacillus subtilis* (processing target of *bacillus* 21). Then *Bacillus subtilis* (processing target of *bacillus* 21) are killed.

Figure 6:
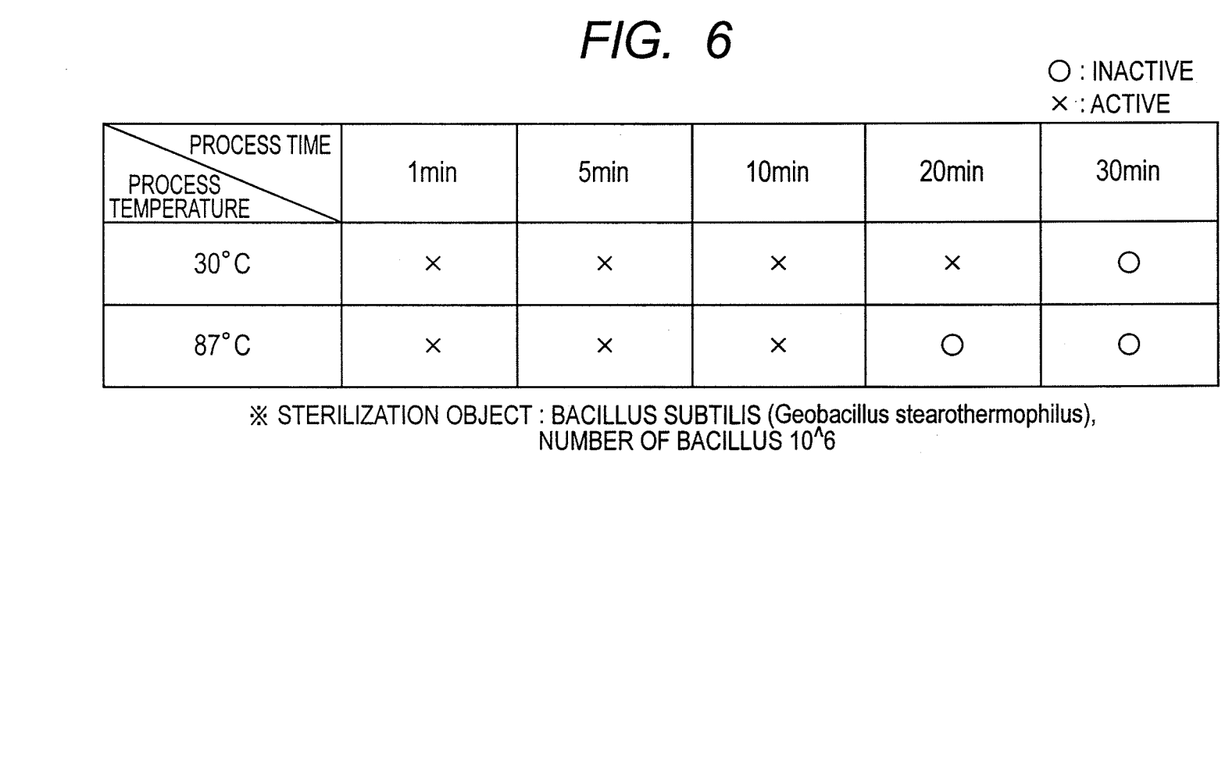

FIG. 5C illustrates a relationship between a irradiation time and a long axis diameter of *bacillus* when *Bacillus subtilis* (processing target of *bacillus* 21) is irradiated with the oxygen plasma. At this time, *Bacillus subtilis* (processing target of *bacillus* 21) is measured at temperatures of 30° C. and 87° C. As a result, this showed that *Bacillus subtilis* (processing target of *bacillus* 21) heated to the temperature of 87° C. shrinks its diameter of *bacillus* faster. The reason is that carbon and oxygen in *Bacillus subtilis* (processing target of *bacillus* 21) have a higher response rate at higher temperature to be removed by the oxygen radical 22 in the oxygen plasma. *Bacillus subtilis* (processing target of *bacillus* 21) halts shrinking the diameter of *bacillus* in the surface layer after the plasma irradiation time of around 10 min. It is because the oxygen radical 22 removes organic material, and then inorganic material, which is inseparable, remains. These matters are also confirmed by *Bacillus subtilis* (processing target of *bacillus* 21) used in this experiment, which keeps active at the temperature of equal to or less than 100° C. and are not killed at the temperature of 87° C. FIG. 6 is an explanatory diagram illustrating a sterilization effect of the oxygen radical 22. *Bacillus subtilis* (processing target of *bacillus* 21) was determined to be active or inactive using a liquid culture medium (TSB culture medium) illustrated in FIG. 5A. The liquid culture medium includes a PH indicator (bromocresol purple). When *Bacillus subtilis* (processing target of *bacillus* 21) is active, PH varies and then color of the liquid culture medium varies. After the plasma irradiation, a culture for 24 hours at 58° C. was carried out. A culture result of *Bacillus subtilis* (processing target of *bacillus* 21) irradiated with oxygen plasma is illustrated in FIG. 6. In the case where *Bacillus subtilis* (processing target of *bacillus* 21) was at the temperature of 87° C., it was confirmed that $10^6$ of *Bacillus subtilis* (processing target of *bacillus* 21) were killed after the process time of 20 minutes. On the other hand, in the case where *Bacillus subtilis* (processing target of *bacillus* 21) is at the temperature of 30° C., killing *Bacillus subtilis* takes the process time of 30 minutes. This confirmed that increasing the temperature of *Bacillus subtilis* (processing target of *bacillus* 21) at plasma irradiation or before plasma irradiation improves sterilization effect.

Figure 7:
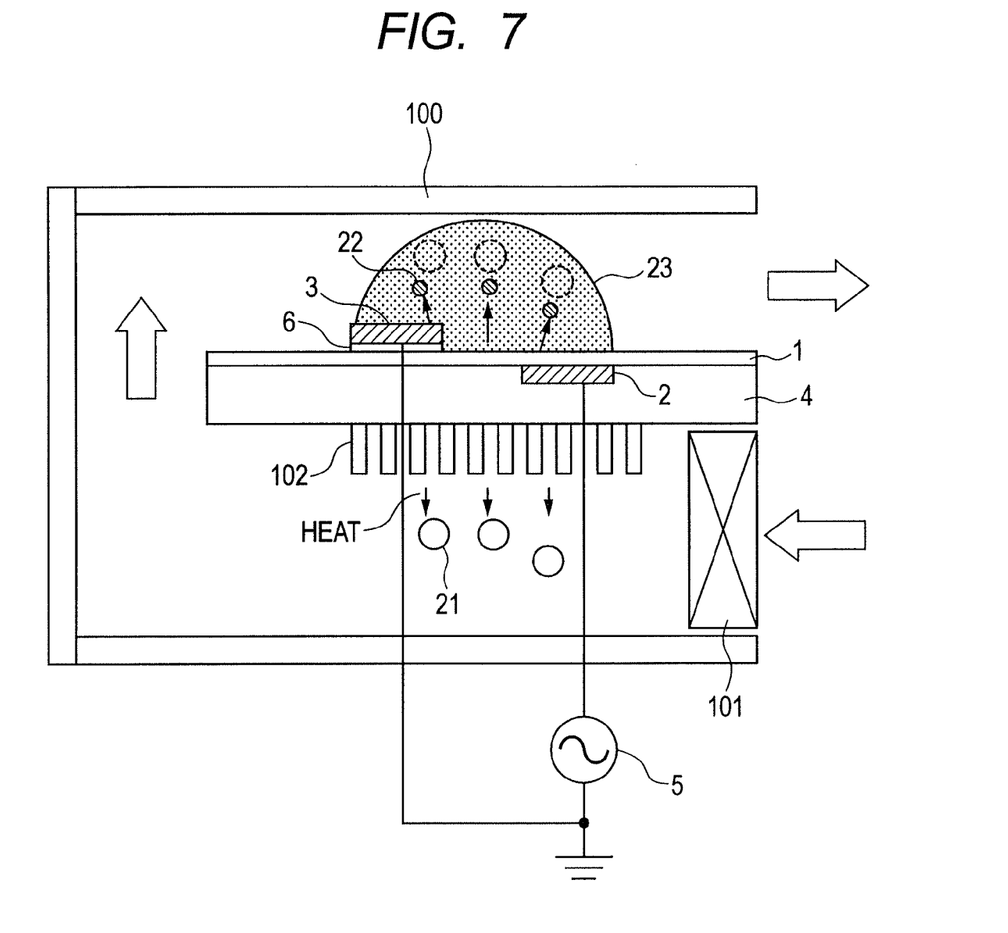

FIG. 7 is a schematic diagram illustrating a configuration of a plasma sterilization apparatus according to the embodiment. FIG. 7 illustrates a device configuration that preheats an air including an airborne *bacillus* (processing target of *bacillus* 21) and sterilizes with the oxygen radical 22. First, the plasma generating portion could be burnt out at high temperature and thus needs to be cooled. In view of this, a fan 101 intakes an air (at atmospheric pressure) including the airborne *bacillus* (processing target of *bacillus* 21) while cooling the plasma generating portion. This heats the air including the airborne *bacillus* (processing target of *bacillus* 21) using thermal radiation of the plasma generating portion. At this time, a radiating fin 102 is provided to effectively transfer heat from the plasma generating portion to the air including the airborne *bacillus* (processing target of *bacillus* 21). Reference numeral 100 designates a housing, and a white arrow designates a direction of airflow.

Then the heated air contacts the plasma 23 and is sterilized by sterile particles in the plasma 23. As the sterile particles, the oxygen radical 22, which is included in the plasma, has larger sterilization effect than that of ozone, which is mainly generated outside the plasma. The structure guides the air to contact the plasma 23 directly. Bringing the air in directly contact with the plasma 23 allows the oxygen radical 22 in the plasma 23 to have an action on the floating *bacillus* (processing target of *bacillus* 21) in the air. The principle will be described in detail referring to FIGS. 8A and 8B. This structure ensures cooling the plasma discharging portion and preheating the airborne *bacillus* (processing target of *bacillus* 21) without a freezing device and a heater. This structure allows use of the oxygen radical 22 as the sterile particles. This ensures sterilization at high speed with a low-cost configuration. The temperature of the heated air varies according to a plasma generating condition and an airflow rate. The air is heated to high temperature by increasing electric power input to the plasma sterilization apparatus while decreasing the airflow rate.

Figure 8A:
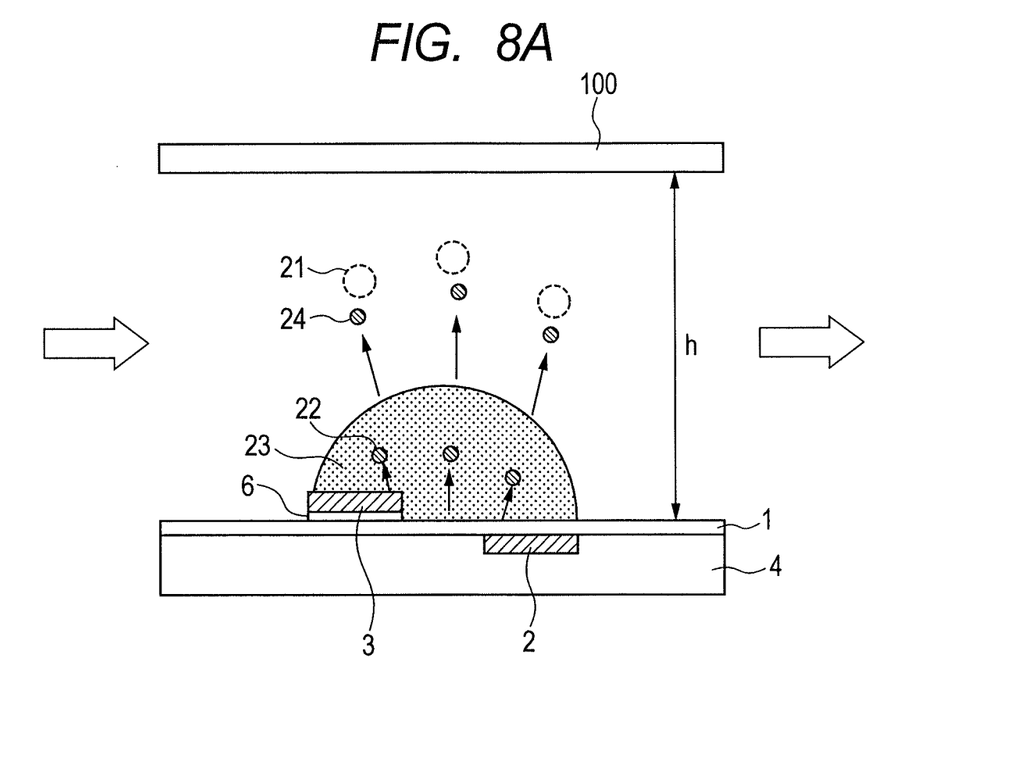
Figure 8B:
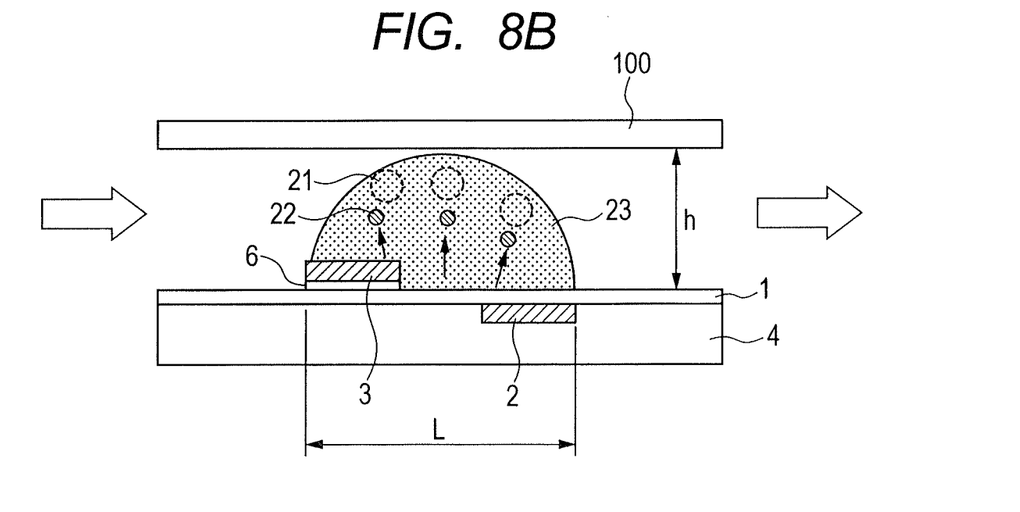

FIGS. 8A and 8B are schematic diagrams illustrating the sterile particles generated in the plasma sterilization apparatus according to the embodiment. When the oxygen radical 22 generated in the plasma diffuses from a plasma generating region, three-body collision with the oxygen molecules occurs. This changes the oxygen radical 22 into ozone 24. Thus, as illustrated in FIG. 8A, in the case where the flow path height h is far larger than the generating region of the plasma 23, the ozone 24 are main sterile particles having action on the airborne *bacillus* (processing target of *bacillus* 21). On the other hand, as illustrated in FIG. 8B, in the case where the flow path height h is within the plasma generating region, the oxygen radical 22 are main sterile particles having a action on the airborne *bacillus* (processing target of *bacillus* 21), which are expected to have large sterilization effect. In order to obtain the sterilization effect by the oxygen radical 22, when a length between both ends of the high-frequency electrode 2 and the earth electrode 3 is defined as a discharge length L, the flow path height h is preferably equal to or less than a half of L ($0 < h \leq (\frac{1}{2})L$).

The above plasma sterilization apparatus was used to sterilize the air in BCR. This achieved sterilization with low electric power at high speed.

In the embodiment, the electrode contacting the plasma 23 is described as the earth electrode 3, and the electrode protected by the dielectric body layer 1 is described as the high-frequency electrode 2. This causes no influence on effects of the embodiment even if the positions of the both electrodes are switched each other.

With the embodiment, the second dielectric body layer (the insulating spacer 6) with a lower permittivity than that of the dielectric body layer between the electrode and the dielectric body layer provides the plasma sterilization apparatus with high plasma generation efficiency. In the plasma generating region, the height of the airflow path may be equal to or less than a half of the electrode distance. This ensures sterilization at high speed.

The above-described embodiment should not be construed in a limiting sense; any modifications are possible without changing the scope of the present invention. For example, the above embodiments are described in detail for ease of describing the present invention. The present invention is not limited to configurations that include the whole elements described above. Replacement of a configuration of one embodiment with a configuration of another embodiment is possible. Addition of a configuration of one embodiment to a configuration of another embodiment is also possible. Addition, removal, and replacement of a part of the configuration among the respective embodiments are also possible.

Industrial Applicability

The present invention is not limited to the application of sterilization in BCR. Application of electrical home appliances such as an air conditioner and a refrigerator, which require to harmlessly sterilize the airborne *bacillus* at low temperature and at high speed. In the present invention, the sterilization effect is described for the airborne *bacillus* (such as a true fungus and a bacteria) as target. Needless to say, an organism such as floating virus in the air may be sterilized.

What is claimed is:

1. A plasma sterilization apparatus comprising:

first and second electrodes;

a first dielectric body layer disposed between the first and second electrodes; and an insulating spacer disposed between the first electrode and the first dielectric body layer, the insulating spacer having a lower permittivity than a permittivity of the first dielectric body layer, wherein:

the insulating spacer is arranged such that at least a portion of the first electrode overlaps with the insulating spacer, as viewed from above, and the insulating spacer is arranged such that the second electrode does not overlap with the insulating spacer, or such that only a portion of the second electrode overlaps with the insulating spacer, as viewed from above.

2. The plasma sterilization apparatus according to claim 1, further comprising an electric power supply configured to supply an alternating voltage between the first and second electrodes, wherein a gap is disposed between the first and second electrodes as a discharge space.

3. The plasma sterilization apparatus according to claim 1, wherein the insulating spacer is configured to reduce a reactive power.

4. The plasma sterilization apparatus according to claim 1, wherein the first electrode includes a projection on a side face of the first electrode so as to reduce a discharge initiation voltage when generating plasma.

5. The plasma sterilization apparatus according to claim 1, wherein the insulating spacer is made of an organic material.

6. The plasma sterilization apparatus according to claim 1, wherein the insulating spacer includes a double sided tape.

7. The plasma sterilization apparatus according to claim 1, wherein the insulating spacer has a width equal to or more than a half of a width of the first electrode.

* * * * *